(12) United States Patent
Abe et al.

(10) Patent No.: US 9,372,179 B2
(45) Date of Patent: Jun. 21, 2016

(54) METHOD FOR MEASURING CHOLESTEROL CONTENT OF CHICKEN EGG BY NON-DESTRUCTIVE MEANS

(71) Applicant: Incorporated Administrative Agency National Agriculture and Food Research Organization, Ibaraki (JP)

(72) Inventors: Hiroyuki Abe, Ibaraki (JP); Masahiro Amari, Ibaraki (JP)

(73) Assignee: National Research and Development Agency National Agriculture and Food Research Organization, Ibaraki (JP)

( * ) Notice: Subject to any disclaimer, the term of this patent is extended or adjusted under 35 U.S.C. 154(b) by 0 days.

(21) Appl. No.: 14/427,488

(22) PCT Filed: Aug. 30, 2013

(86) PCT No.: PCT/JP2013/073278
§ 371 (c)(1),
(2) Date: Mar. 11, 2015

(87) PCT Pub. No.: WO2014/042016
PCT Pub. Date: Mar. 20, 2014

(65) Prior Publication Data
US 2015/0226720 A1    Aug. 13, 2015

(30) Foreign Application Priority Data

Sep. 13, 2012 (JP) ................................. 2012-201727
Nov. 14, 2012 (JP) ................................. 2012-250210

(51) Int. Cl.
*G01J 5/02* (2006.01)
*G01N 33/08* (2006.01)
(Continued)

(52) U.S. Cl.
CPC .............. *G01N 33/08* (2013.01); *G01N 21/359* (2013.01); *G01N 21/55* (2013.01); *G01N 21/59* (2013.01); *G01N 2201/129* (2013.01)

(58) Field of Classification Search
CPC . G01N 21/35; G01N 21/359; G01N 21/3504; G01J 3/02; G01J 3/42
See application file for complete search history.

(56) References Cited

U.S. PATENT DOCUMENTS

| | | | | |
|---|---|---|---|---|
| 5,520,938 A | * | 5/1996 | Brunnquell | ............ A01K 43/00 119/6.8 |
| 2002/0075476 A1 | * | 6/2002 | Chalker, II | ............ A01K 43/00 356/53 |

(Continued)

FOREIGN PATENT DOCUMENTS

| JP | 2001-133404 | 5/2001 |
|---|---|---|
| JP | 2004-516475 | 6/2004 |

(Continued)

OTHER PUBLICATIONS

Yoritaka, Aoyama, Tamago no Eiyou (Egg Nutrition), 1998, Ryo Nakamura (ed.), Tamago no Kagaku (Egg Science), Asakura Publishing Co., Ltd. (Tokyo), pp. 42-53.

(Continued)

*Primary Examiner* — David Porta
*Assistant Examiner* — Mamadou Faye
(74) *Attorney, Agent, or Firm* — McCarter & English (57) ABSTRACT

This invention provides a means for measuring a cholesterol content of a chicken egg by a non-destructive means. This invention relates to a method for measuring a cholesterol content of a chicken egg comprising: a step of light irradiation of irradiating the chicken egg with light in the visible to near-infrared wavelength range; a step of light detection of detecting light radiated from the chicken egg caused by that the light irradiated in the step of light irradiation is transmitted through the chicken egg or reflected inside the chicken egg; a step of spectrum acquisition of acquiring a near-infrared spectrum of the light detected in the step of light detection; and a step of cholesterol content determination of determining a cholesterol content of the chicken egg on the basis of the near-infrared spectrum acquired in the step of spectrum acquisition.

12 Claims, 9 Drawing Sheets

(51) Int. Cl.
*G01N 21/359* (2014.01)
*G01N 21/55* (2014.01)
*G01N 21/59* (2006.01)

(56) References Cited

U.S. PATENT DOCUMENTS

2007/0215050 A1* 9/2007 Hebrank .............. A01K 45/007
119/6.8
2008/0221415 A1 9/2008 Sweeney

FOREIGN PATENT DOCUMENTS

JP 2010-273682 12/2010
WO 02/083848 10/2002

OTHER PUBLICATIONS

Hatta, Hajime, "The Nutritional and Physiological Function of Eggs", Foods & Food Ingredients Journal of Japan, 2006, vol. 211, No. 11, pp. 908-917 (with English Summary).

Oh, Suk Y, et al., "Effect of Dietary Egg on Variability of Plasma Cholesterol Levels and Lipoprotein Cholesterol", The American Journal of Clinical Nutrition, Sep. 1985, vol. 42, pp. 421-431.

Herron, Kristin L., et al., "Men Classified as Hypo- or Hyper-responders to Dietary Cholesterol Feeding Exhibit Differences in Lipoprotein Metabolism", The Journal of Nutrition, 2002, vol. 133, pp. 1036-1042.

Teramoto, Tamio, "Japan Atherosclerosis Society (JAS) Guidelines for Prevention of Altherosclerotic Cardiovascular Diseases", Japan Atherosclerosis Society, 2007, pp. 1-21 (with English Summary).

Fujiwara, K., et al., "Effect of Fermented Soybean, "Natto" on the Production and Qualities of Chicken Meat", Asian-Australasian Journal of Animal Science, Dec. 2008, vol. 21, No. 12, pp. 1766-1772.

Official Methods of Analysis of the Association of Official Analytical Chemists, Chapter 17—Eggs and Egg Products, 1970, Issue 11, pp. 283-286.

Shen, Chih-Shang, J., et al., "Enzymatic Determination of Cholesterol in Egg Yolk", Journal of Association of Official Analytical Chemists, 1982, vol. 65, No. 5, pp. 1222-1224.

Abe, Hiroyuki, et al., "Non-destructive Determination of Egg-Cholesterol by Near Infrared (NIR) Spectroscopy", Japanese Journal of Zootechnical Science, Aug. 25, 2013, vol. 84, No. 1, pp. 77-80 (with English Summary).

Zotte, Antonella Dalle, et al., "The Use of Near-Infrared Reflectance Spectroscopy (NIRS) in the Prediction of Chemical Composition of Freeze-Dried Egg Yolk and Discrimination Between Different n-3 PUFA Feeding Sources", Animal Feed Science and Technology, May 28, 2006, vol. 128, Issues 1-2, pp. 108-121.

International Search Report based on International Application No. PCT/JP2013/073278, dated Sep. 25, 2013.

* cited by examiner

METHOD FOR MEASURING CHOLESTEROL CONTENT OF CHICKEN EGG BY NON-DESTRUCTIVE MEANS

TECHNICAL FIELD

The present invention relates to a method for measuring a cholesterol content of a chicken egg by a non-destructive means.

BACKGROUND ART

Chicken eggs are known to be excellent foods that have well-balanced amino acid compositions and contain lipids. In addition, chicken eggs and fish eggs are both known to be foods with high cholesterol content. It is said that the cholesterol content of a chicken egg is 1,300 to 1,400 mg per 100 g of egg yolk on average and 450 to 500 mg per 100 g of a whole egg (an edible part) on average. According to the average values above, a chicken egg contains about 230 mg of cholesterol (Non-Patent Document 1).

It is said that most cholesterol (80% or more) in the human body is not derived from food but rather is biosynthesized in the human body. As dietary cholesterol intake increases, in general, the mechanism for suppressing cholesterol biosynthesis in the body is activated, and cholesterol homeostasis in the blood is maintained. Thus, according to the mainstream way of thinking, a healthy individual does not need to pay much attention to the dietary cholesterol intake from chicken eggs (Non-Patent Document 2).

It is known that some persons easily reflect dietary cholesterol intake in their blood cholesterol levels (those who are referred to as "hyper-responders") while others do not (those who are referred to as "hypo-responders") (Non-Patent Documents 3 and 4). During the treatment of hyperlipidemia, the upper limit of the amount of cholesterol that a patient is allowed to ingest in a day may be determined to be approximately 300 mg (Non-Patent Document 5). Accordingly, it is important to know the cholesterol content of food materials, such as chicken eggs, for the purpose of keeping the amount of cholesterol ingested within an adequate range.

As a method for regulating the cholesterol level of a chicken egg, for example, a method of feeding dry natto to a chicken is known (Non-Patent Document 6). In the case of usual chicken eggs, however, cholesterol levels are known to vary significantly among individuals, such as from about 1,000 mg to more than 1,800 mg per 100 g of egg yolk. Therefore, a means that enables measurement of the cholesterol content of a chicken egg in a simple manner has been desired.

For example, Non-Patent Document 7 discloses, as a method for measuring the cholesterol content of a chicken egg, a method comprising deproteinization of egg yolk or whole egg, extraction of a cholesterol-containing fraction, and analysis of the cholesterol content in the extract via high-performance liquid chromatography (hereafter, it may be referred to as "HPLC"). Also, Non-Patent Document 8 discloses an enzymatic method of measuring the cholesterol content in the cholesterol-containing extract with the use of cholesterol oxidase or catalase.

When a measurement sample is prepared by breaking the target chicken egg as described in the aforementioned documents, the target chicken egg cannot be used as a food material. In order to measure the cholesterol content of a chicken egg to be used as a food material, accordingly, it is necessary that the measurement be carried out by a non-destructive means. As an example of a method for characterizing features of a chicken egg by a non-destructive means, Patent Document 1 discloses a method of processing eggs having identified characteristics comprising steps of: irradiating an egg with light from a light source, wherein the light includes light in both the visible and infrared wavelength ranges; receiving light transmitted through each egg with a detector positioned adjacent to each egg; generating a spectrum for each egg that represents light intensity at a plurality of the visible and infrared wavelength regions; and comparing the generated spectrum for each egg with a spectrum associated with a live egg to identify live eggs.

PRIOR ART DOCUMENTS

Patent Documents

Patent Document 1: JP Patent Publication 2010-273682 A

Non-Patent Documents

Non-Patent Document 1: Yoritaka Aoyama, *Tamago no Eiyou* (Egg Nutrition), 1998, Ryo Nakamura (ed.), *Tamago no Kagaku* (Egg Science), pp. 42-53, Asakura Publishing, Co., Ltd. (Tokyo)

Non-Patent Document 2: Hajime Hatta, *Tamago no Eiyou Kinou to Seiri Kinou* (Nutritional and Biological Functions of Eggs), 2006, Foods & Foods Ingredients Journal of Japan, Volume 211, pp. 908-917)

Non-Patent Document 3: Oh S Y, Miller L T, 1985, Effect of dietary egg on variability of plasma cholesterol levels and lipoprotein cholesterol, American Journal of Clinical Nutrition, Volume 42, pp. 421-431

Non-Patent Document 4: Herron K L, Vega-Lopes S, Conde K, Ramjiganesh T, Schchter N S, Fernandez M L, 2003, Men classified as hypo- or hyper-responders to dietary cholesterol feeding exhibit differences in lipoprotein metabolism, Journal of Nutrition, Volume 133, pp. 1036-1042

Non-Patent Document 5: Japan Atherosclerosis Society, 2007, Guidelines for Prevention of Atherosclerotic Cardiovascular Diseases, 2007, Kyowa Kikaku Ltd., Tokyo Non-Patent Document 6: Fujiwara K, Miyaguchi Y, Toyoda A, Nakamura Y, Yamazaki M, Nakashima K, Abe H, 2008, Effect of fermented soybean "natto" supplement on egg production and qualities, Asian-Australasian Journal of Animal Science, Volume 21, pp. 1610-1615

Non-Patent Document 7: Official Methods of Analysis of AOAC, Issue 11, Washington, 1970

Non-Patent Document 8: Shen C S, Chen I S, Sheppard A J, 1982, Enzymatic determination of cholesterol in egg yolk, Journal of Association of Official Analytical Chemists, Volume 65, pp. 1222-1224

SUMMARY OF THE INVENTION

Objects to be Attained by the Invention

If the cholesterol content of a chicken egg can be measured by a non-destructive means before it is sold in a store, information concerning the cholesterol content of each chicken egg can be provided to a consumer at the time of sales in a store. When chicken eggs are cooked at home, raw egg is mainly used as a food material. Accordingly, information concerning the cholesterol content of each chicken egg is useful for the management of the dietary cholesterol intake.

In general, chicken eggs are subjected to washing, candling, grading, and packaging at a GP (grading and packaging) center. If the cholesterol content of a chicken egg is measured by a non-destructive means within a short period of time when an egg is subjected to the aforementioned processing at the GP center, accordingly, the cholesterol content of each chicken egg may be determined, and a chicken egg may be efficiently selected based on the determined cholesterol content.

As a technique of characterizing features of a chicken egg by a non-destructive means, the method disclosed in Patent Document 1 is known. However, Patent Document 1 does not disclose a means for measuring the cholesterol content of a chicken egg.

Therefore, it was an object of the present invention to provide a non-destructive means for measuring the cholesterol content of a chicken egg.

Means for Attaining the Objects

The present inventors have conducted concentrated studies concerning means for attaining the above objects. As a result, the present inventors have discovered that the cholesterol content of a chicken egg could be quantified with high accuracy without breaking the egg by irradiating the chicken egg with near-infrared light in a particular wavelength range and detecting the light transmitted through the egg. This has led to the completion of the present invention.

Specifically, the present invention is summarized as follows.

(1) A method for measuring a cholesterol content of a chicken egg comprising:

a step of light irradiation of irradiating the chicken egg with light in the visible to near-infrared wavelength range;

a step of light detection of detecting light radiated from the chicken egg caused by that the light irradiated in the step of light irradiation is transmitted through the chicken egg or reflected inside the chicken egg;

a step of spectrum acquisition of acquiring a near-infrared spectrum of the light detected in the step of light detection; and a step of cholesterol content determination of determining a cholesterol content of the chicken egg on the basis of the near-infrared spectrum acquired in the step of spectrum acquisition.

(2) The method according to (1), wherein the light irradiated in the step of light irradiation is in the wavelength range of 600 to 1,100 nm.

(3) The method according to (1) or (2), wherein the light irradiated in the step of light irradiation is irradiated to a chicken egg positioned so as to align a plane containing a long-axis line connecting the rounded end to the pointed end to be parallel to a horizontal plane, in a direction orthogonal to the long-axis line, so that the light is passed through an egg yolk of the chicken egg on a plane parallel to the horizontal plane containing the long-axis line, and the light detected in the step of light detection is radiated in a downward direction from the chicken egg caused by that the light is transmitted through the chicken egg positioned so as to align a plane containing a long-axis line connecting the rounded end to the pointed end to be parallel to the horizontal plane, and the light being radiated in a direction orthogonal to the long-axis line so as to be passed through the egg yolk of the chicken egg on a plane parallel to the vertical plane containing the long-axis line.

(4) An apparatus for measuring a cholesterol content of a chicken egg comprising:

a light irradiation means that irradiates the chicken egg with light in the visible to near-infrared wavelength range;

a light detection means that detects light radiated from the chicken egg caused by that the light irradiated by the light irradiation means is transmitted through the chicken egg or reflected inside the chicken egg;

a spectrum acquisition means that acquires a near-infrared spectrum of the light detected by the light detection means; and a cholesterol content determination means that determines a cholesterol content of the chicken egg on the basis of the near-infrared spectrum acquired by the spectrum acquisition means.

(5) The apparatus according to (4), wherein the light irradiated by the light irradiation means is in the wavelength range of 600 to 1,100 nm.

(6) The apparatus according to (4) or (5), wherein the light irradiation means is disposed so as to irradiate light to a chicken egg positioned so as to align a plane containing a long-axis line connecting the rounded end to the pointed end to be parallel to a horizontal plane, in a direction orthogonal to the long-axis line, so that the light is passed through an egg yolk of the chicken egg on a plane parallel to the horizontal plane containing the long-axis line, and the light detection means is disposed so as to detect light radiated in a downward direction from the chicken egg caused by that the light is transmitted through the chicken egg positioned so as to align a plane containing a long-axis line connecting the rounded end to the pointed end to be parallel to the horizontal plane, and the light being radiated in a direction orthogonal to the long-axis line so as to be passed through the egg yolk of the chicken egg on a plane parallel to the vertical plane containing the long-axis line.

Effects of the Invention

According to the present invention, a means for measuring a cholesterol content of a chicken egg by a non-destructive means can be provided.

This description includes part or all of the content as disclosed in the descriptions and/or drawings of Japanese Patent Application Nos. 2012-201727 and 2012-250210, which are priority documents of the present application.

EMBODIMENTS FOR CARRYING OUT THE INVENTION

Hereafter, preferable embodiments of the present invention are described in detail.

In this description, the characteristic features of the present invention are described with reference to figures as appropriate. In the figures, dimensions and configurations of elements are exaggerated for clarification, and real dimensions and configurations are not accurately provided. Accordingly, the technical scope of the present invention is not limited to dimensions and configurations of the elements provided in the figures.

1. Method for Measuring Cholesterol Content of Chicken Egg

The present invention relates to a method for measuring a cholesterol content of a chicken egg.

Near-infrared spectroscopy comprising irradiating a sample with near-infrared light in a particular wavelength range and detecting transmitted or reflected light therefrom allows analysis of the inside of a sample without breaking the sample. Thus, near-infrared spectroscopy is employed for inspection or analysis of a food material or a processed food product, such as characteristic survey of a chicken egg (e.g., Patent Document 1), measurement of a sugar content of fruit, measurement of a starch content of rice or wheat, or component analysis of soy sauce. However, no methods for measuring a cholesterol content of a chicken egg via near-infrared spectroscopy had been known.

The present inventors have discovered that a cholesterol content of a chicken egg could be quantified with high accuracy by irradiating the chicken egg with near-infrared light in a particular wavelength range and detecting a transmitted light therefrom. The method of the present invention is carried out by irradiating a sample chicken egg with near-infrared light from the outside of the eggshell. Thus, the cholesterol content of a chicken egg can be measured without breaking the egg by the method of the present invention.

The method of the present invention can be extensively applied to chicken eggs that are used as food materials. For example, chicken eggs obtained from layer chickens that are usually used in the art can be used, regardless of the variety of a layer chicken and/or the timing of egg collection. In general, the color of chicken eggs provided as food materials is not limited to white, and some chicken eggs have colored eggshells, such as brown or reddish-brown eggshells. The method of the present invention can be applied to chicken eggs with either white or colored eggshells.

Figure 1:
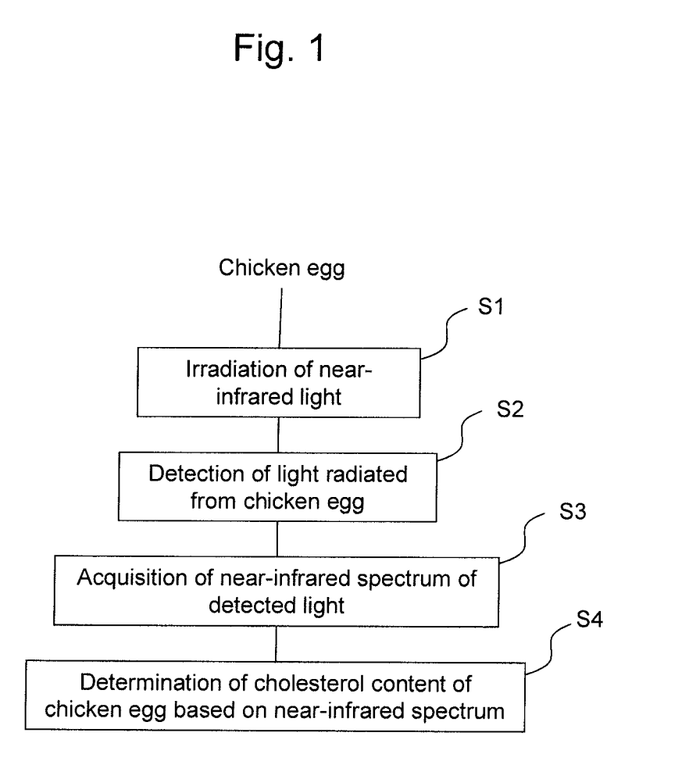
FIG. 1 shows a scheme of an embodiment of the method according to the present invention.

FIG. 1 shows a scheme of an embodiment of measurement of a cholesterol content of a chicken egg according to the present invention. Hereafter, preferable embodiments of the method of the present invention are described in detail with reference to FIG. 1.

[1-1. Step of Light Irradiation]

It is necessary that the method of the present invention comprise a step of light irradiation (Step S1) of irradiating a chicken egg with light in the visible to near-infrared wavelength range.

In general, the term "visible light" refers to light in a wavelength range from 400 nm to 750 nm and the term "near-infrared light" refers to light in a wavelength range from 750 nm to 2,500 nm. The term "light in the visible to near-infrared wavelength range" used herein refers to light in a wavelength range from 400 nm to 2,500 nm. The light irradiated in this step (hereafter, it may be referred to as "irradiation light") is in a wavelength range preferably from 400 nm to 1,100 nm, and more preferably from 600 nm to 1,100 nm. With the irradiation of light in a wavelength range from 400 nm to 1,100 nm, the wavelength sweep range can be narrowed, and the time required for the implementation of the step can be shortened. With the use of light in a wavelength range of 600 nm or more, also, the cholesterol content can be determined with high accuracy on the basis of a near-infrared spectrum described below.

In this step, irradiation light can be irradiated to a chicken egg from any direction. For example, irradiation light can be irradiated to a chicken egg positioned so as to align a plane containing a long-axis line connecting the rounded end to the pointed end to be parallel to the horizontal plane, in a direction orthogonal to the long-axis line, so that the light is passed through an egg yolk of the chicken egg from the top of the chicken egg on a plane parallel to the vertical plane containing the long-axis line. It is preferable that irradiation light be irradiated to a chicken egg positioned so as to align a plane containing a long-axis line connecting the rounded end to the pointed end to be parallel to the horizontal plane, in a direction orthogonal to the long-axis line, so that the light is passed through an egg yolk of the chicken egg on a plane parallel to the horizontal plane containing the long-axis line. In general, this step is carried out while the chicken egg is in a fixed state, so as to realize the positional relationship between the chicken egg and the irradiation light as described above. To this end, it is preferable that a chicken-egg-fixing member be used in this step in order to position a chicken egg as described above. When a chicken-egg-fixing member is used, a chicken egg is mounted on top of the chicken-egg-fixing member. The chicken-egg-fixing member is disposed so as to be in contact with the underside of the chicken egg. Thus, the amount of the irradiated light that is reflected inside the chicken egg may vary between a portion that is in contact with the chicken-egg-fixing member and a portion that is not in contact therewith. By irradiating a chicken egg with light on a plane parallel to the horizontal plane containing a long-axis line connecting the rounded end to the pointed end, accordingly, influence of the chicken-egg-fixing member can be suppressed. In general, cholesterol is mainly contained in an egg yolk of a chicken egg. By irradiating light in a direction orthogonal to the long-axis line so as to be passed through an egg yolk of a chicken egg, and the cholesterol content of the chicken egg can be measured with higher accuracy.

The term "parallel," "vertical," or "orthogonal" used herein refers to a positional relationship in which lines and/or planes are completely or nearly completely parallel, vertical, or orthogonal to each other.

In this description, the phrase "the light is passed through an egg yolk" refers to a situation in which light is passed through at least a part of an egg yolk of a chicken egg. Accordingly, the location from which light is passed through an egg yolk is, for example, at a distance of 20 to 60 mm, and typically 27 to 52 mm, from the pointed end of a chicken egg.

It is preferable that this step be performed by irradiating light inside a housing member that accommodates a chicken egg and a chicken-egg-fixing member. The housing member is preferably a part such as a dark box, which is capable of substantially blocking light from outside. By performing this step inside the housing member, the influence of light from outside can be substantially suppressed, and the cholesterol content of a chicken egg can be measured with higher accuracy.

[1-2. Step of Light Detection]

It is necessary that the method of the present invention comprise a step of light detection (Step S2) comprising detecting light radiated from the chicken egg caused by that the light irradiated in the step of light irradiation (Step S1) is transmitted through the chicken egg or reflected inside the chicken egg.

The light detected in this step is in a wavelength range preferably from 400 nm to 1,100 nm, and more preferably from 600 nm to 1,100 nm. By detecting light in a wavelength range from 400 nm to 1,100 nm, the wavelength sweep range can be narrowed, and the time required for the implementation of the step can be shortened. With the use of light in a wavelength range of 600 nm or more, also, the cholesterol content can be determined with high accuracy on the basis of the near-infrared spectrum described below.

In this step, light radiated from a chicken egg in various directions can be detected. For example, light to be detected may be radiated in a lateral direction from a chicken egg caused by that the light is transmitted through the chicken egg positioned so as to align a plane containing a long-axis line connecting the rounded end to the pointed end to be parallel to the horizontal plane, and the light being radiated in a direction orthogonal to the long-axis line so as to be passed through an egg yolk of the chicken egg on a plane parallel to the horizontal plane containing the long-axis line. Alternatively, light to be detected may be radiated in an upward direction from a chicken egg caused by that the light is reflected inside the chicken egg positioned so as to align a plane containing a long-axis line connecting the rounded end to the pointed end to be parallel to the horizontal plane, and the light being radiated in a direction orthogonal to the long-axis line so as to be passed through an egg yolk of the chicken egg on a plane parallel to the vertical plane containing the long-axis line. However, the light to be detected in this step may preferably be radiated in a downward direction from a chicken egg caused by that the light is transmitted through the chicken egg positioned so as to align a plane containing a long-axis line connecting the rounded end to the pointed end to be parallel to the horizontal plane, and the light being radiated in a direction orthogonal to the long-axis line so as to be passed through an egg yolk of the chicken egg on a plane parallel to the vertical plane containing the long-axis line. The light irradiated in the step of light irradiation is not only transmitted through a chicken egg (hereafter, it may be referred to as a "transmitted light"), but also reflected inside the chicken egg (hereafter, it may be referred to as a "reflected light"). As described above, a reflected light may be influenced by a chicken-egg-fixing member. When a transmitted light that is radiated in a lateral direction from a chicken egg is to be detected, the irradiation light may be influenced by light caused by that the irradiation light is scattered outside the chicken egg (hereafter, it may be referred to as an "light scattered outside"). When a transmitted light that is radiated in a downward direction from a chicken egg is to be detected, in contrast, the unfavorable influence described above can be substantially suppressed. Accordingly, the light radiated in a downward direction from a chicken egg caused by that the light is transmitted through the chicken egg positioned so as to align a plane containing a long-axis line connecting the rounded end to the pointed end to be parallel to the horizontal plane on a plane parallel to the vertical plane containing the long-axis line may be detected, so that the influence caused by the reflected light and/or light scattered outside can be suppressed. Also, the light radiated in a direction orthogonal to the long-axis line so as to be passed through an egg yolk of the chicken egg positioned as described above may be detected, so that the cholesterol content of the chicken egg can be measured with higher accuracy.

It is preferable that this step be performed by detecting light inside the housing member described above. By performing this step inside the housing member, the influence of light from outside can be substantially suppressed, and the cholesterol content of a chicken egg can be measured with higher accuracy.

[1-3. Step of Spectrum Acquisition]

It is necessary that the method of the present invention comprise a step of spectrum acquisition (Step S3) of acquiring a near-infrared spectrum of the light detected in the step of light detection (Step S2).

This step is performed by generating a near-infrared spectrum on the basis of the light detected in the step of light detection. As a means for generating a near-infrared spectrum, a near-infrared spectrometer that is commonly used in the art is preferable. With the use of a near-infrared spectrometer, a highly accurate near-infrared spectrum can be generated within a short period of time.

[1-4. Step of Cholesterol Content Determination]

It is necessary that the method of the present invention comprise a step of cholesterol content determination (Step S4) of determining a cholesterol content of a chicken egg on the basis of the near-infrared spectrum acquired in the step of spectrum acquisition (Step S3).

In this step, a technique of chemometrics that is known in the art can be employed as a means for determining a cholesterol content of a chicken egg on the basis of the near-infrared spectrum. When the technique of chemometrics is employed, a calibration curve is prepared in advance in the manner described below. The step of spectrum acquisition is carried out with the use of multiple (preferably 50 or more) chicken eggs for the preparation of a calibration curve, so as to acquire a near-infrared spectrum. Subsequently, chicken eggs are broken and the content of cholesterol in a chicken egg component is measured by a means known in the art. Examples of the means for measurement include colorimetry involving the use of an enzyme, such as cholesterol oxidase or catalase, and instrumental analysis involving the use of a chromatography technique, such as HPLC, LC-MS, or GC-MS. Colorimetry using an enzyme is preferable from the viewpoint of convenience. Thereafter, the analysis data is obtained from the near-infrared spectrum, and the calibration curve is then prepared on the basis of the cholesterol content measured above. Examples of means for analysis employed for the preparation of a calibration curve include partial least square (PLS) regression analysis comprising extracting a plurality of potential factors so as to adjust covariance between a linear function of X and Y to the maximal level and multiple regression analysis. PLS regression analysis reflects results of weighting originating from components, and thus estimation accuracy becomes high, and/or overfitting does not occur. Accordingly, PLS regression analysis is preferable. Analysis of near-infrared spectral data and preparation of a calibration curve as described above may be performed manually with the use of an arithmetic device, such as a personal computer, or such procedures may be performed with the use of commercially available chemometrics software that is common in the art.

The calibration curve is prepared in the manner described above, and the cholesterol content of a target chicken egg can then be determined with the use of the prepared calibration curve by the analytical means as described above. A calibration curve may be prepared each time that this step is carried out. However, it is preferable that the prepared data be stored in an arithmetic device and the calibration curve be retrieved from the device at the time of measurement. Thus, the duration of measurement of the cholesterol content can be shortened.

The accuracy of the calibration curve prepared in the manner described above can be evaluated in the manner described below. The step of spectrum acquisition is carried out with the use of multiple (preferably 50 or more) chicken eggs for the evaluation of a calibration curve, so as to acquire a near-infrared spectrum. On the basis of the near-infrared spectrum, the cholesterol content is estimated based on the calibration curve prepared in the manner described above. Subsequently, chicken eggs are broken and the content of cholesterol in a chicken egg component is measured by a means known in the art. By comparing the estimated cholesterol content with the measured cholesterol content, the accuracy of the calibration curve is evaluated. When a calibration curve is prepared via PLS regression analysis, the accuracy of the calibration curve can be evaluated by, for example, a method in which the ratio of a standard deviation of a value measured by a conventional technique to a standard error from the regression estimate (SECV), RPD (the ratio of standard deviation of reference data in predicted sample set to SECV; SD/SECV), is used as an index (Williams, P C., 2001, Implementation of near-infrared technology, "Near-Infrared Technology in the Agricultural and Food Industries," 2nd Ed., pp. 145-169, Williams, P C and Norris K H (ed.), American Association of Cereal Chemist Press, St. Paul, Minn.). When the RPD value attained by near-infrared spectroscopy is 2.5 or less, in general, analysis accuracy is evaluated as being insufficient. An RPD value of 2.5 to 3.0 is evaluated as being applicable to rough analysis, and an RPD value of 3.0 to 5.0 is evaluated as being applicable to highly accurate screening.

The method of the present invention enables measurement of a cholesterol content of a chicken egg with very high accuracy. When the calibration curve is prepared by PLS regression analysis in the step of cholesterol content determination, for example, the RPD value attained by the method of the present invention is at least 3. According to the method of the present invention, therefore, the cholesterol content of a chicken egg can be determined with high accuracy, so that highly accurate screening can be carried out.

2. Apparatus for Measuring Cholesterol Content of Chicken Egg

The present invention also relates to an apparatus for measuring a cholesterol content of a chicken egg.

Figure 2:
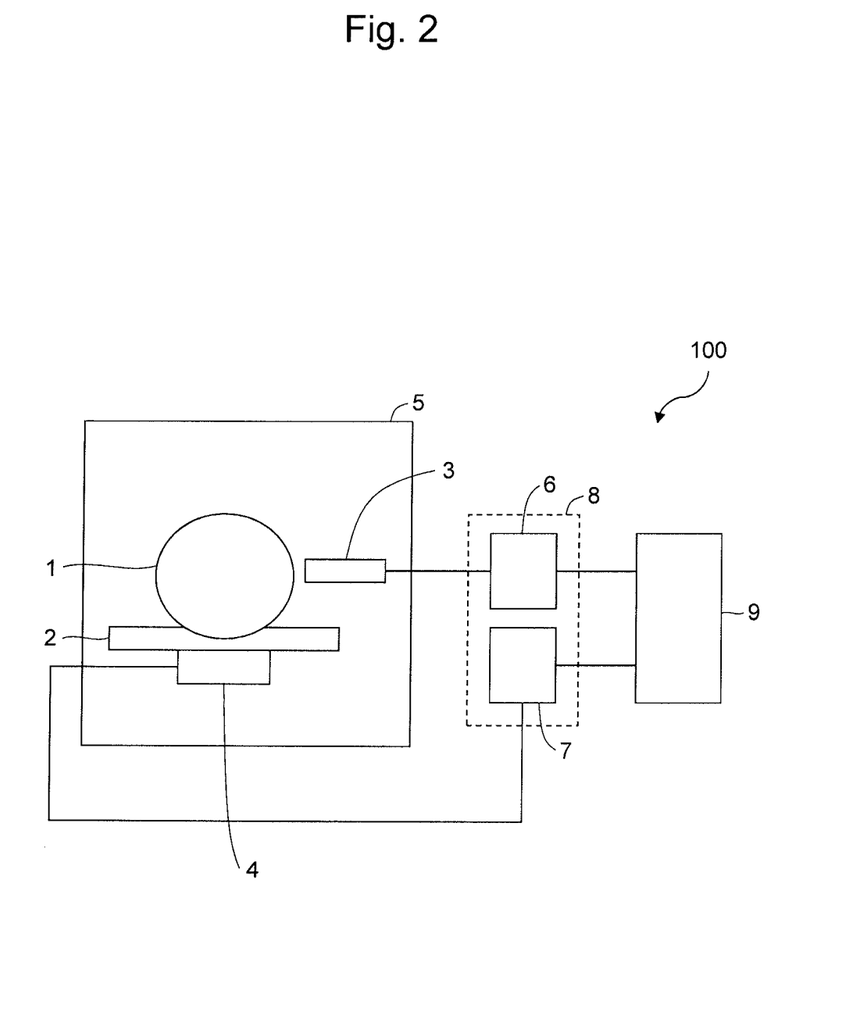
FIG. 2 shows a constitution of an embodiment of the apparatus for measuring a cholesterol content of a chicken egg according to the method of the present invention.

FIG. 2 shows a constitution of an embodiment of an apparatus for measuring a cholesterol content of a chicken egg according to the method of the present invention. As shown in FIG. 2, it is necessary that the apparatus 100 of the present invention comprise: a light irradiation means 3 that irradiates a chicken egg 1 with light in the visible to near-infrared wavelength range; a light detection means 4 that detects light radiated from the chicken egg 1 caused by that the light irradiated by the light irradiation means 3 is transmitted through the chicken egg 1 or reflected inside the chicken egg 1; a spectrum acquisition means that acquires a near-infrared spectrum of the light detected by the light detection means 4; and a cholesterol content determination means that determines a cholesterol content of the chicken egg 1 on the basis of the near-infrared spectrum acquired by the spectrum acquisition means. With the use of the apparatus having the constitution as described above, the method for measuring a cholesterol content of a chicken egg of the present invention can be implemented.

It is preferable that the apparatus 100 of the present invention comprise a chicken-egg-fixing member 2. In the apparatus 100 of the present invention, the chicken egg 1 is mounted on top of the chicken-egg-fixing member 2, so that the underside of the chicken egg 1 is brought into contact with the chicken-egg-fixing member 2. It is preferable that the chicken egg 1 be mounted on top of the chicken-egg-fixing member 2, so that a plane containing a long-axis line connecting the rounded end to the pointed end is aligned so as to be parallel to the horizontal plane. By comprising the chicken-egg-fixing member 2, the chicken egg 1 can preferably be positioned as described above while the near-infrared spectrum is obtained with the use of the apparatus of the present invention. Thus, the accuracy of a cholesterol content of a chicken egg measured with the use of the apparatus of the present invention can be improved.

It is preferable that the apparatus 100 of the present invention comprise a housing member 5 that accommodates the chicken egg 1, the chicken-egg-fixing member 2, the light irradiation means 3, and the light detection means 4. The housing member 5 is preferably, a part such as a dark box that is capable of substantially blocking light from outside. By accommodating the members and the means described above inside the housing member 5, the influence of light from outside can be substantially suppressed, and the cholesterol content of a chicken egg can be measured with higher accuracy.

The light irradiation means 3 is preferably a light irradiation element selected from the group consisting of a halogen lamp, a light-emitting diode (LED), and an EverGlo ceramic material. For example, the light irradiation means 3 is connected to a light source 6 through, for example, an optical fiber cable or other means. The light source 6 is used to oscillate light in the desired wavelength range as described above. The irradiation light may be scattered by the light source 6 or by the light irradiation means 3.

The light detection means 4 is preferably a light-detecting element selected from the group consisting of silicon, PbS (lead sulfide), InGaAs (indium/gallium/arsenic), and arsenide. The light detection means 4 is connected to a detector 7 through, for example, an optical fiber cable or other means. The detector 7 is used to detect light in the desirable wavelength range described above.

A spectrum acquisition means is an apparatus comprising a detector 7, and it is used to generate a near-infrared spectrum on the basis of the light detected by the light detection means 4. It is preferable that the spectrum acquisition means be a spectrometer 8 comprising a light source 6, in addition to the detector 7, such as a near-infrared spectrometer used in common in the art.

It is preferable that the cholesterol content determination means be an arithmetic device 9 comprising a storage part that stores spectral data acquired by the spectrum acquisition means and an arithmetic processing part that performs the analysis described above on the basis of the spectral data.

When measuring a cholesterol content of a chicken egg with the use of the apparatus of the present invention, a light irradiation means and a light detection means can be disposed in various positional relationships with respect to the chicken egg. FIGS. 3 to 6 each schematically show an embodiment of the use of the apparatus according to the present invention.

Figure 3:
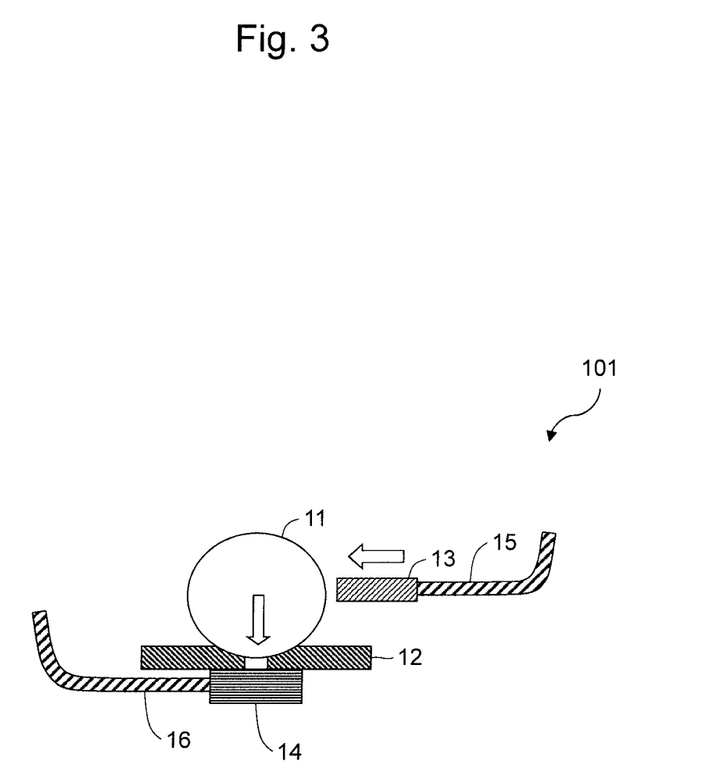
FIG. 3 schematically shows an embodiment of the use of the apparatus for measuring a cholesterol content of a chicken egg according to the method of the present invention.

As shown in FIG. 3, the apparatus 101 of the present invention may comprise: the light irradiation means 13 disposed so as to irradiate light to the chicken egg 11 positioned so as to align a plane containing a long-axis line connecting the rounded end to the pointed end to be parallel to the horizontal plane, in a direction orthogonal to the long-axis line, so that the light is passed through an egg yolk of the chicken egg 11 on a plane parallel to the horizontal plane containing the long-axis line; and the light detection means 14 disposed so as to detect light radiated in a downward direction from the chicken egg 11 caused by that the light is transmitted through the chicken egg 11 positioned so as to align a plane containing a long-axis line connecting the rounded end to the pointed end to be parallel to the horizontal plane, and the light being radiated in a direction orthogonal to the long-axis line so as to be passed through the egg yolk of the chicken egg 11 on a plane parallel to the vertical plane containing the long-axis line (hereafter, it is also referred to as the "first embodiment"). In this embodiment, a chicken-egg-fixing member 12 is disposed so as to be brought into contact with the underside of the chicken egg 11, and the light irradiation means 13 and the light detection means 14 are connected to a light source and a detector through optical fiber cables 15 and 16, respectively. The chicken-egg-fixing member 12 is preferably provided with a through-hole to detect the light radiated in a downward direction from the chicken egg 11 with the aid of the light detection means 14.

Figure 4:
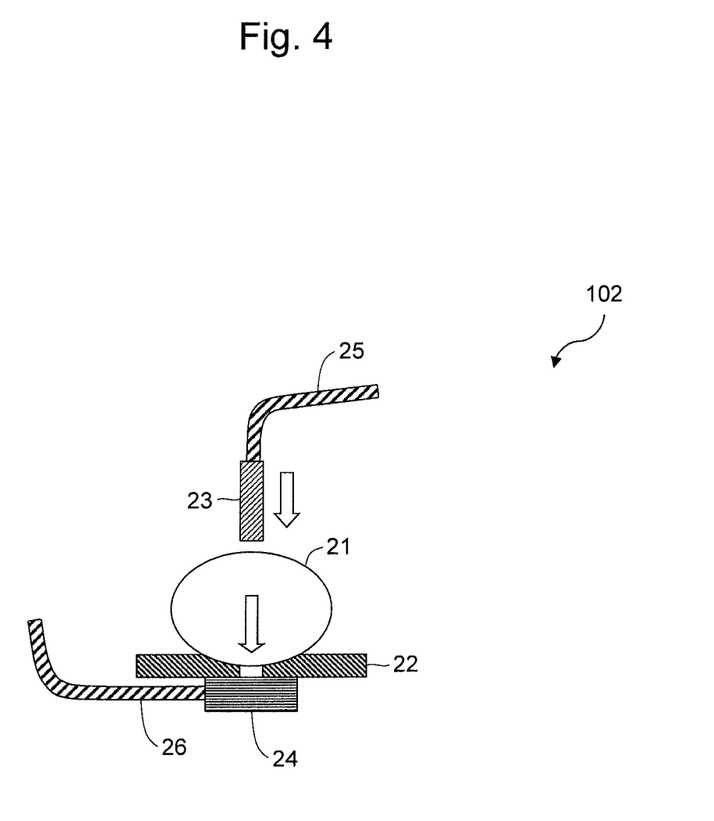
FIG. 4 schematically shows another embodiment of the use of the apparatus for measuring a cholesterol content of a chicken egg according to the method of the present invention.

As shown in FIG. 4, also, the apparatus 102 of the present invention may comprise: the light irradiation means 23 disposed so as to irradiate light to the chicken egg 21 positioned so as to align a plane containing a long-axis line connecting the rounded end to the pointed end to be parallel to the horizontal plane, in a direction orthogonal to the long-axis line, so that the light is passed through an egg yolk of the chicken egg 21 from the top of the chicken egg 21 on a plane parallel to the vertical plane containing the long-axis line; and the light detection means 24 disposed so as to detect light radiated in a downward direction from the chicken egg 21 caused by that the light is transmitted through the chicken egg 21 positioned so as to align a plane containing a long-axis line connecting the rounded end to the pointed end to be parallel to the horizontal plane, and the light being radiated in a direction orthogonal to the long-axis line so as to be passed through the egg yolk of the chicken egg 21 on a plane parallel to the vertical plane containing the long-axis line (hereafter, it is also referred to as the "second embodiment"). In this embodiment, a chicken-egg-fixing member 22 is disposed so as to be brought into contact with the underside of the chicken egg 21, and the light irradiation means 23 and the light detection means 24 are connected to a light source and a detector through optical fiber cables 25 and 26, respectively. The chicken-egg-fixing member 22 is preferably provided with a through-hole to detect the light radiated in a downward direction from the chicken egg 21 with the aid of the light detection means 24.

Figure 5:
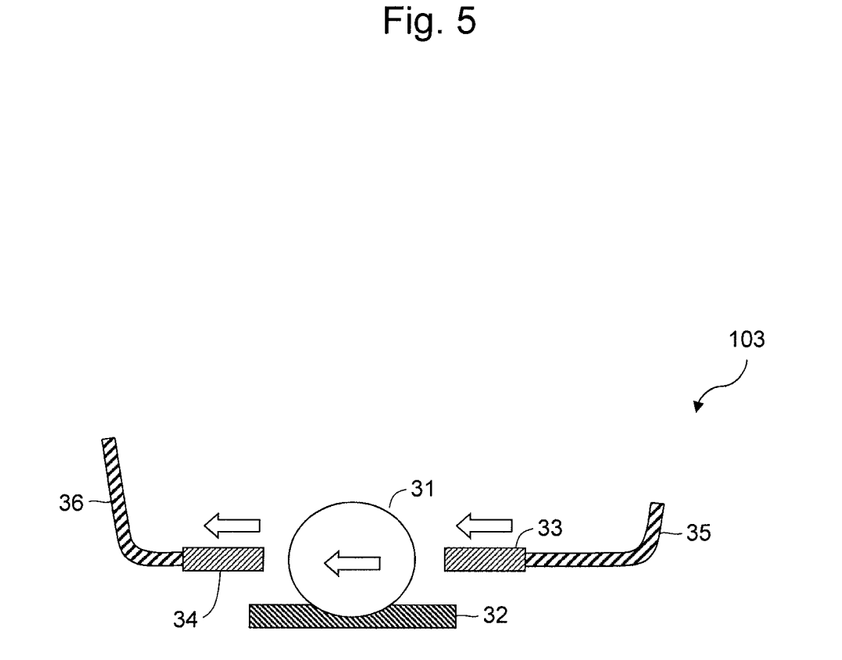
FIG. 5 schematically shows a further embodiment of the use of the apparatus for measuring a cholesterol content of a chicken egg according to the method of the present invention.

As shown in FIG. 5, further, the apparatus 103 of the present invention may comprise: the light irradiation means 33 disposed so as to irradiate light to the chicken egg 31 positioned so as to align a plane containing a long-axis line connecting the rounded end to the pointed end to be parallel to the horizontal plane, in a direction orthogonal to the long-axis line, so that the light is passed through an egg yolk of the chicken egg 31 on a plane parallel to the horizontal plane containing the long-axis line; and the light detection means 34 disposed so as to detect light radiated in a lateral direction from the chicken egg 31 caused by that the light is transmitted through the chicken egg 31 positioned so as to align a plane containing a long-axis line connecting the rounded end to the pointed end to be parallel to the horizontal plane, and the light being radiated in a direction orthogonal to the long-axis line so as to be passed through the egg yolk of the chicken egg 31 on a plane parallel to the horizontal plane containing the long-axis line (hereafter, it is also referred to as the "third embodiment"). In this embodiment, a chicken-egg-fixing member 32 is disposed so as to be brought into contact with the underside of the chicken egg 31, and the light irradiation means 33 and the light detection means 34 are connected to a light source and a detector through optical fiber cables 35 and 36, respectively.

Figure 6:
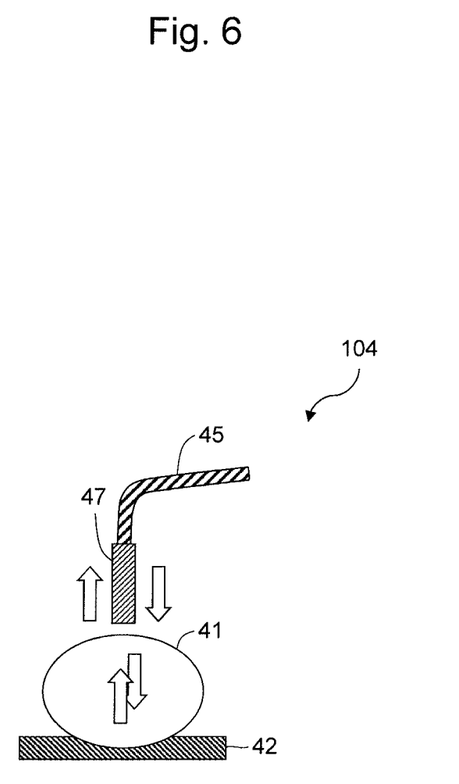
FIG. 6 schematically shows a still further embodiment of the use of the apparatus for measuring a cholesterol content of a chicken egg according to the method of the present invention.

As shown in FIG. 6, alternatively, the apparatus 104 of the present invention may comprise: the light irradiation means disposed so as to irradiate light to the chicken egg 41 positioned so as to align a plane containing a long-axis line connecting the rounded end to the pointed end to be parallel to the horizontal plane, in a direction orthogonal to the long-axis line, so that the light is passed through an egg yolk of the chicken egg 41 from the top of the chicken egg 41 on a plane parallel to the vertical plane containing the long-axis line; and the light detection means disposed so as to detect light radiated in an upward direction from the chicken egg 41 caused by that the light is reflected inside the chicken egg 41 positioned so as to align a plane containing a long-axis line connecting the rounded end to the pointed end to be parallel to the horizontal plane, and the light being radiated in a direction orthogonal to the long-axis line so as to be passed through the egg yolk of the chicken egg 41 on a plane parallel to the vertical plane containing the long-axis line (hereafter, it is also referred to as the "fourth embodiment"). In this embodiment, a chicken-egg-fixing member 42 is disposed so as to be brought into contact with the underside of the chicken egg 41. While the light irradiation means and the light detection means may be provided as separate elements, as shown in FIG. 6, these means are preferably provided in the form of a single means 47 for light irradiation and detection. In such case, the means 47 for light irradiation and detection is connected to a light source and a spectroscopy/detector through an optical fiber cable 45.

When measuring a cholesterol content of a chicken egg using the method of the present invention, as described above, measurement accuracy can vary depending on positional relationships of the light irradiation means and the light detection means relative to a chicken egg. The present inventors have discovered that the cholesterol content could be measured with high accuracy when measuring a cholesterol content of a chicken egg with the use of the first embodiment of the apparatus according to the present invention among the 4 types of embodiments described above. Therefore, the first embodiment of the apparatus according to the present invention is preferable.

As described in detail above, the cholesterol content of a chicken egg can be quantified with high accuracy without breaking the egg with the application of the method and the apparatus of the present invention. According to the present invention, therefore, the cholesterol content of each chicken egg may be determined, and a chicken egg may be efficiently selected based on the cholesterol content determined at the GP center.

EXAMPLES

Hereafter, the present invention is described in greater detail with reference to the examples, although the technical scope of the present invention is not limited to these examples.

[Apparatus for Measuring Near-Infrared Spectrum]

The near-infrared spectrometer (Model 6500, NIR Systems Inc.; current name: Foss NIR Systems, Inc.) was used in the following experiment. FIG. 3 schematically shows measurement of the cholesterol content of a chicken egg using the apparatus described above. As shown in FIG. 3, in the apparatus 101 a chicken egg 11 was mounted on a sample-fixing table 12, so that a plane containing a long-axis line connecting the rounded end to the pointed end would be aligned so as to be parallel to the horizontal plane. The light irradiation element 13 was disposed so as to irradiate light to the chicken egg 11 in a direction orthogonal to a long-axis line connecting the rounded end to the pointed end thereof, so that the light would be passed through an egg yolk of the chicken egg 11 on a plane parallel to the horizontal plane containing the long-axis line of the chicken egg 11. The light detection element 14 was disposed so as to detect light radiated in a downward direction from the chicken egg 11 caused by that the light would be transmitted through the chicken egg 11, and the light being radiated in a direction orthogonal to the long-axis line connecting the rounded end to the pointed end of the chicken egg 11 so as to be passed through the egg yolk of the chicken egg 11 on a plane parallel to the vertical plane containing the long-axis line. The sample-fixing table 12 was provided with a through-hole to detect the light radiated in a downward direction from the chicken egg 11 with the aid of the light detection element 14. The light irradiation element 13 and the light detection element 14 were connected to a light source and a detector provided outside a dark box through optical fiber cables 15 and 16, respectively.

[Measurement of Near-Infrared Spectrum]

The following experiment was carried out using 57 chicken eggs (egg weight: 52 g to 60 g) produced by White Leghorn hens (58-week-old) raised at the Institute of Livestock and Grassland Science of the National Agriculture and Food Research Organization.

Figure 7:
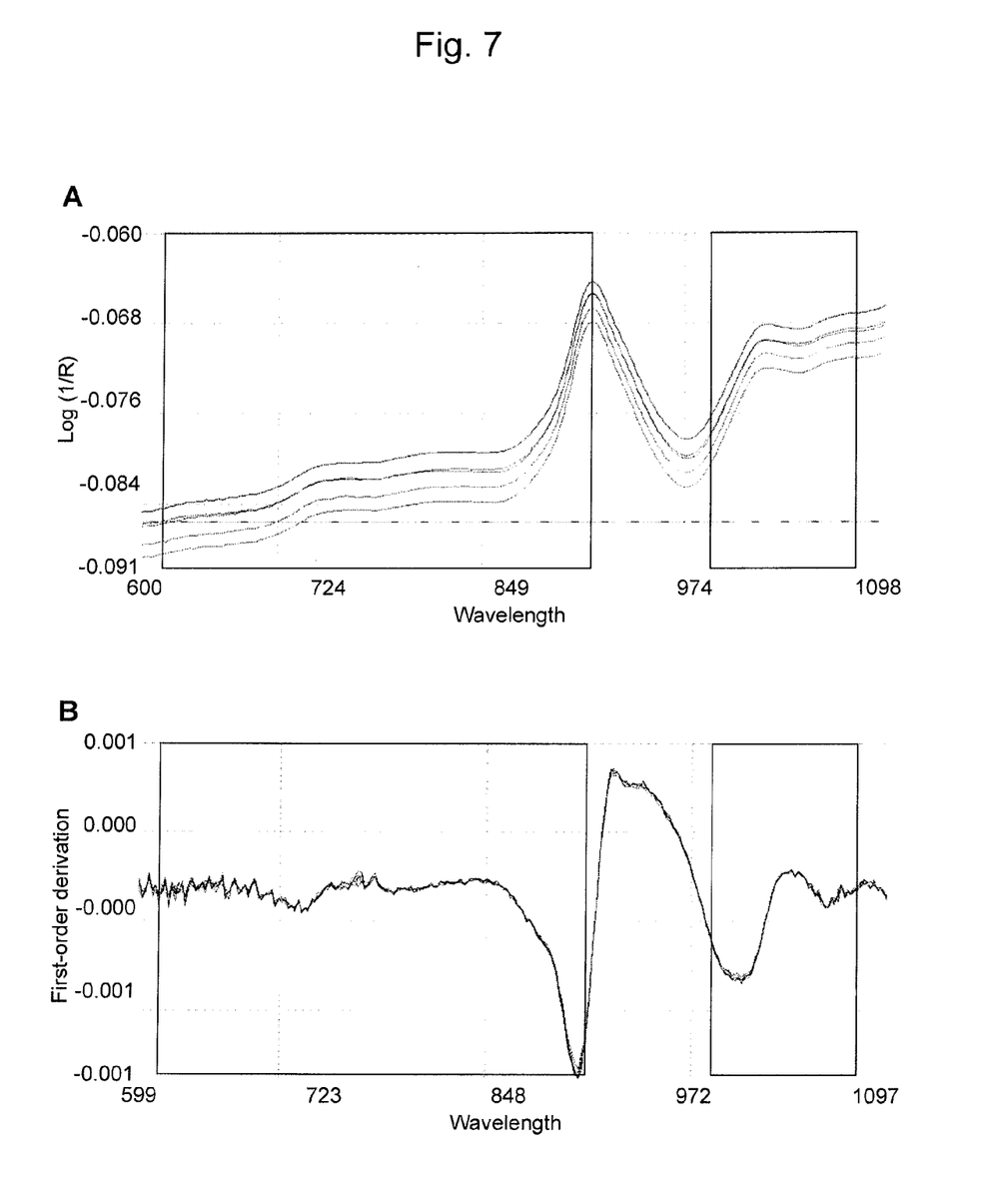
FIG. 7 shows near-infrared spectra of a chicken egg obtained by the method of the present invention. A: Original spectra of the near-infrared spectra; and B: A first-order derivation of spectra obtained through first-order derivation processing of the original spectra.

At the outset, the weight of each chicken egg was determined. A chicken egg was mounted on a sample-fixing table provided in a dark box of the near-infrared spectrometer described above. The dark box was closed, and the chicken egg was irradiated with light in the visible to near-infrared wavelength range (i.e., 400 nm to 1,100 nm) with the use of the light irradiation element provided on the lateral side of the chicken egg. The transmitted light radiated in a downward direction from the chicken egg was detected with the use of the light detection element provided on the lower side of the through-hole on the sample-fixing table. On the basis of the detected light that had been transmitted, a near-infrared spectrum in the visible to near-infrared wavelength range (i.e., 400 nm to 1,100 nm) was acquired. Following the measurement, the chicken egg was revolved 90 degrees around an axis line connecting the rounded end to the pointed end, and another near-infrared spectrum was acquired in the same manner as described above. Thus, two near-infrared spectra were acquired for a single chicken egg. The duration of measurement for a single near-infrared spectrum was approximately 1.5 minutes. FIG. 7A shows original near-infrared spectra and FIG. 7B shows a first-order derivation of spectra obtained through first-order derivation processing of the original spectra.

[Measurement of Cholesterol Content by Conventional Technique]

Following the near-infrared spectral measurement, the chicken egg was broken, an eggshell, an egg white, and an egg yolk were separated from each other, and these parts were separately weighed. With the use of a mixture of 5 ml of a methanol solution containing 1.0 M potassium hydroxide and 2.5 ml of isopropyl alcohol, a lipophilic fraction was extracted from 0.25 mg of the egg yolk. The obtained lipophilic fraction was heated at 70° C. for 30 minutes, so as to saponify fatty acids. A specific volume of the saponified fraction was prepared using a volumetric flask. In accordance with a conventional technique (Non-Patent Document 8), the cholesterol content in the saponified lipophilic fraction was determined using a colorimetric assay kit with the use of cholesterol oxidase or catalase (F-kit cholesterol, Roche). The cholesterol content per 100 g of egg yolk was determined based on the egg yolk weight. The cholesterol content per chicken egg was also determined based on a value obtained by multiplying the cholesterol content per 100 g of egg yolk by the weight of the egg yolk.

[Preparation of Cholesterol Calibration Curve Via Regression Analysis]

Figure 8:
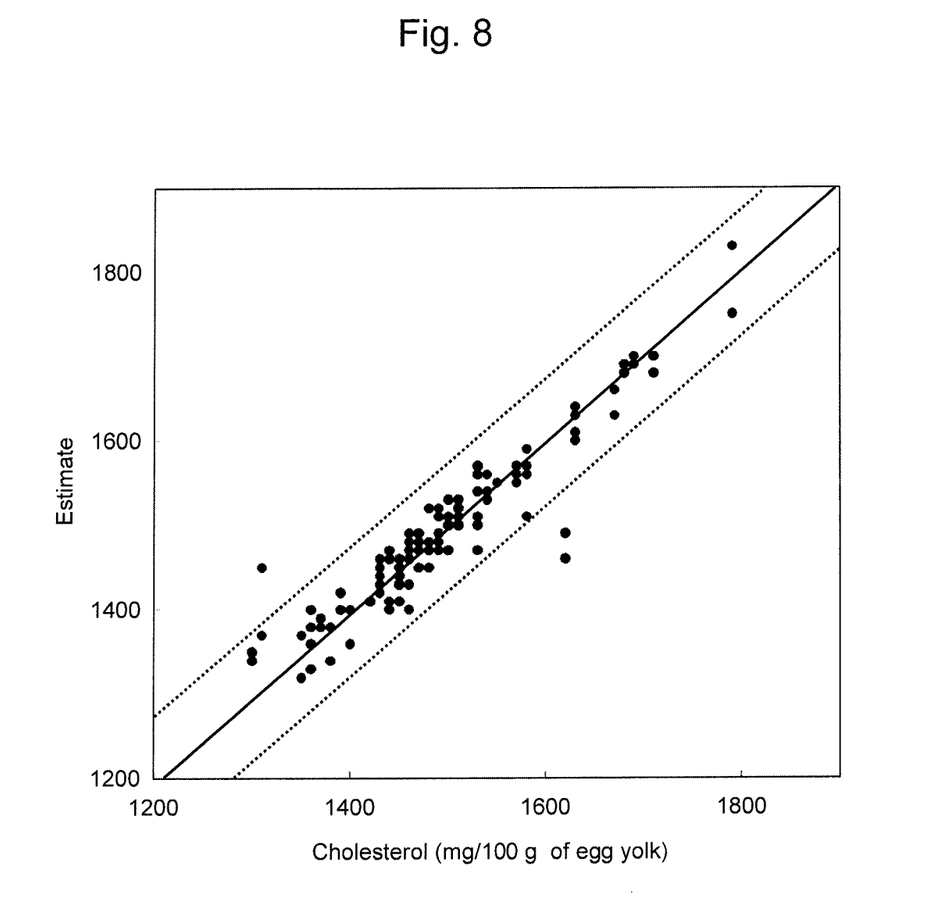
FIG. 8 shows a correlation between measured values of the cholesterol content per 100 g of egg yolk measured by a conventional technique and estimated values of the cholesterol content estimated by the method of the present invention. In the figure, a solid line indicates a regression line and a dotted line indicates the 95% confidence interval.
Figure 9:
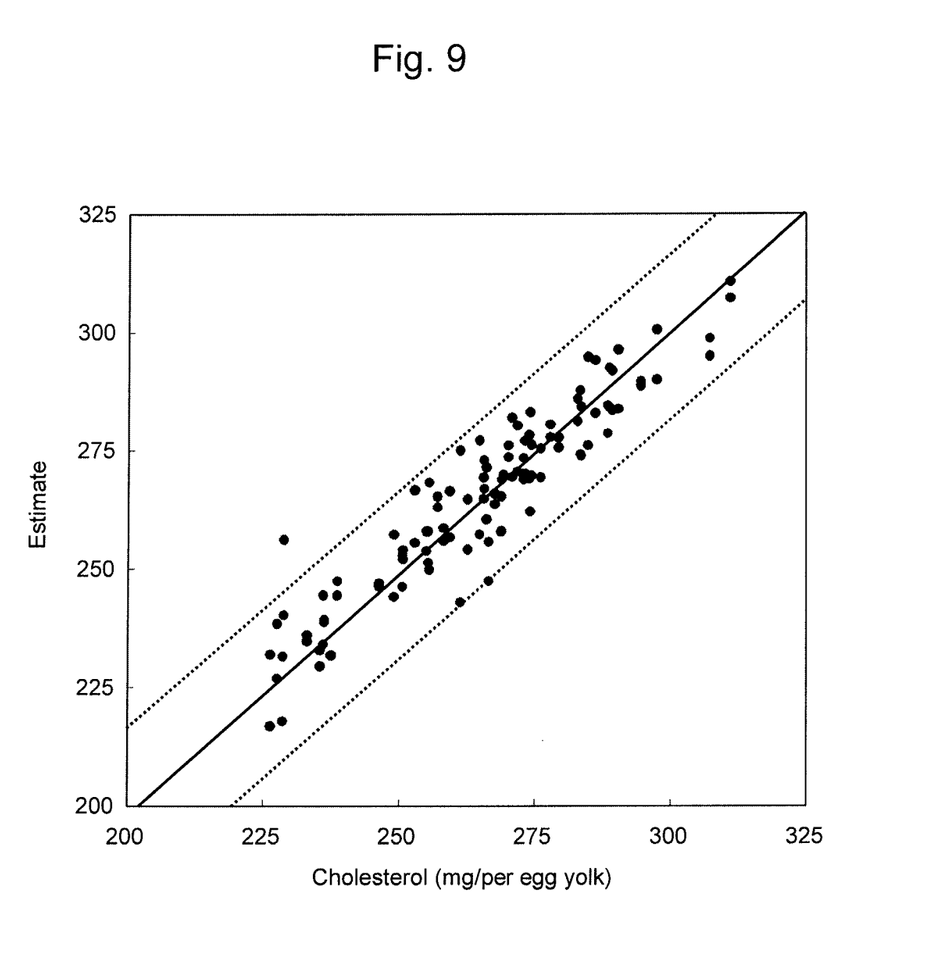
FIG. 9 shows a correlation between measured values of the cholesterol content per chicken egg measured by a conventional technique and estimated values of the cholesterol content estimated by the method of near-infrared spectroscopy of the present invention. In the figure, a solid line indicates a regression line and a dotted line indicates the 95% confidence interval.

Of the two near-infrared spectra acquired in the manner described above, the first-order derivatives in the wavelength ranges of 614 nm to 946 nm and 984 nm to 1,054 nm were used to prepare calibration curves. Calibration curves were prepared by partial least square (PLS) regression analysis comprising extracting a plurality of potential factors so as to adjust covariance between a linear function of X and Y to the maximal level. The accuracy of the prepared calibration curves was estimated via cross-validation. The contribution ratio of the cholesterol content measured by the conventional technique mentioned above to the value attained via near infrared quantitative analysis ($RSQ=r^2$) and the standard error (SECV) from the regression estimate were determined. With the method in which the ratio of a standard deviation of a value measured by a conventional technique to SECV, RPD (the ratio of standard deviation of reference data in predicted sample set to SECV; SD/SECV) is used as an index, the accuracy of the quantitative analysis was evaluated based on the prepared calibration curves (Williams, P C., 2001, Implementation of near-infrared technology, "Near-Infrared Technology in the Agricultural and Food Industries," 2nd Ed., pp. 145-169, Williams, P C and Norris K H (ed.), American Association of Cereal Chemist Press, St. Paul, Minn.). FIG. 8 shows a correlation between measured values of the cholesterol content per 100 g of egg yolk measured by a conventional technique and estimated values of the cholesterol content estimated by near-infrared spectroscopy according to the present invention. FIG. 9 shows a correlation between measured values of the cholesterol content per chicken egg measured by a conventional technique and estimated values of the cholesterol content estimated by near-infrared spectroscopy according to the present invention. In these figures, a solid line indicates a regression line and a dotted line indicates the 95% confidence interval.

As shown in FIG. 8, the measured values of the cholesterol content per 100 g of egg yolk measured by a conventional technique was highly correlated with the estimated values of the cholesterol content estimated by near-infrared spectroscopy according to the present invention. The contribution ratio was 0.885, the standard error of calibration was 33, and RPD was 3.00. As shown in FIG. 9, also, the measured values of the cholesterol content per chicken egg measured by a conventional technique was highly correlated with the estimated values of the cholesterol content estimated by near-infrared spectroscopy according to the present invention. In this case, the contribution ratio was 0.893, the standard error of calibration was 7.117, and RPD was 3.08.

When the RPD value attained by near-infrared spectroscopy is 2.5 or less, in general, analysis accuracy is evaluated as insufficient. An RPD value of 2.5 to 3.0 is evaluated as applicable to rough analysis, and that of 3.0 to 5.0 is evaluated as applicable to highly accurate screening. According to the method of the present invention, the RPD value was within a range of 3.0 to 5.0, as described above. Therefore, the method of the present invention is evaluated as applicable to highly accurate screening.

All publications, patents, and patent applications cited herein are incorporated herein by reference in their entirety.

DESCRIPTION OF NUMERAL REFERENCES 100, 101, 102, 103 . . . : Apparatus for measuring cholesterol content of chicken egg
1, 11, 21, 31, 41 . . . : Chicken egg
2, 12, 22, 32, 42 . . . : Chicken-egg-fixing member
3, 13, 23, 33 . . . : Light irradiation means
4, 14, 24, 34 . . . : Light detection means
5 . . . : Housing member
6 . . . : Light source
7 . . . : Detector
8 . . . : Spectrometer
9 . . . : Arithmetic device
15, 25, 35, 45, 16, 26, 36 . . . : Optical fiber cable
47 . . . : Means for light irradiation and detection

We claim:

1. A method for measuring a cholesterol content of a chicken egg comprising:
   irradiating the chicken egg with light in the visible to near-infrared wavelength range;
   detecting light radiated from the chicken egg caused by the irradiated light being transmitted through the chicken egg or reflected inside the chicken egg;
   acquiring a near-infrared spectrum of the light detected; and
   determining a cholesterol content of the chicken egg on the basis of the near-infrared spectrum acquired with the use of a calibration curve,
   wherein the irradiated light is irradiated to the chicken egg positioned so as to align a plane containing a long-axis line connecting the rounded end of the egg to the pointed end of the egg to be parallel to a horizontal plane, in a direction orthogonal to the long-axis line, so that the light is passed through an egg yolk of the chicken egg on a plane parallel to the horizontal plane containing the long-axis line, and
   the detected light is the light radiated in a downward direction from the chicken egg caused by the light transmitted through the chicken egg positioned so as to align a plane containing a long-axis line connecting the rounded end of the egg to the pointed end of the egg to be parallel to the horizontal plane, and the light being radiated in a direction orthogonal to the long-axis line so as to be passed through the egg yolk of the chicken egg on a plane parallel to the vertical plane containing the long-axis line.

2. The method according to claim 1, wherein the irradiated light is in the wavelength range of 600 to 1,100 nm.

3. An apparatus for measuring a cholesterol content of a chicken egg comprising:
   a light irradiation means that irradiates the chicken egg with light in the visible to near-infrared wavelength range;
   a light detection means that detects light radiated from the chicken egg caused by the irradiated light being transmitted through the chicken egg or reflected inside the chicken egg;
   a spectrum acquisition means that acquires a near-infrared spectrum of the light detected; and
   a cholesterol content determination means that determines a cholesterol content of the chicken egg on the basis of the near-infrared spectrum acquired with the use of a calibration curve,
   wherein the light irradiation means is disposed so as to irradiate light to a chicken egg positioned so as to align a plane containing a long-axis line connecting the rounded end of the egg to the pointed end of the egg to be parallel to a horizontal plane, in a direction orthogonal to the long-axis line, so that the light is passed through an egg yolk of the chicken egg on a plane parallel to the horizontal plane containing the long-axis line, and
   the light detection means is disposed so as to detect light radiated in a downward direction from the chicken egg caused by that the light is transmitted through the chicken egg positioned so as to align a plane containing a long-axis line connecting the rounded end of the egg to the pointed end of the egg to be parallel to the horizontal plane, and the light being radiated in a direction orthogonal to the long-axis line so as to be passed through the egg yolk of the chicken egg on a plane parallel to the vertical plane containing the long-axis line.

4. The apparatus according to claim 3, wherein the irradiated light is in the wavelength range of 600 to 1,100 nm.

5. An apparatus for measuring a cholesterol content of a chicken egg comprising:
   a housing;
   a light source in the housing that irradiates the chicken egg with light in the visible to near-infrared wavelength range;
   a fixing member in the housing for mounting the chicken egg;
   a detector in the housing that detects light radiated from the chicken egg caused by the irradiated light being transmitted through the chicken egg or reflected inside the chicken egg;
   a spectrometer that acquires a near-infrared spectrum of the light detected; and
   an arithmetic device that determines a cholesterol content of the chicken egg on the basis of the near-infrared spectrum acquired with the use of a calibration curve,
   wherein the chicken egg positioned so as to align a plane containing a long-axis line connecting the rounded end of the egg to the pointed end of the egg to be parallel to a horizontal plane,
   wherein the light source irradiates the chicken egg in a direction orthogonal to the long-axis line so that the light is passed through an egg yolk of the chicken egg on a plane parallel to the horizontal plane containing the long-axis line, and
   wherein the detector detects light radiated in a direction orthogonal to the long-axis line so that the light is passed through the egg yolk of the chicken egg on a plane parallel to the vertical plane containing the long-axis line.

6. The apparatus according to claim 5, wherein the irradiated light is in the wavelength range of 600 to 1,100 nm.

7. The method according to claim 1, wherein the calibration curve is prepared each time of determining the cholesterol content.

8. The method according to claim 1, wherein the calibration curve is retrieved from an arithmetic device which stores data prepared beforehand.

9. The apparatus according to claim 3 further comprising a calibration curve preparation means that prepares the calibration curve each time the cholesterol content is determined.

10. The apparatus according to claim 3 further comprising a calibration curve retrieval means that retrieves the calibration curve from an arithmetic device which stores data prepared beforehand.

11. The apparatus according to claim 5, wherein the arithmetic device prepares the calibration curve each time the cholesterol content is determined.

12. The apparatus according to claim 5, wherein the arithmetic device retrieves the calibration curve therefrom which stores data prepared beforehand.

* * * * *